US012685532B2

(12) United States Patent
Zhang et al.

(10) Patent No.: US 12,685,532 B2
(45) Date of Patent: Jul. 21, 2026

(54) OPEN LINEAR STAPLER

(71) Applicant: Cilag GmbH International, Zug (CH)

(72) Inventors: Jie Zhang, Shanghai (CN); Junjie Wang, Shanghai (CN); Xiangchun Hong, Shanghai (CN); Joshua Uth, Mason, OH (US); Anil K. Nalagatla, Mason, OH (US); Bingshi Wang, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/851,254

(22) PCT Filed: Apr. 5, 2023

(86) PCT No.: PCT/IB2023/053477
§ 371 (c)(1),
(2) Date: Sep. 26, 2024

(87) PCT Pub. No.: WO2023/194932
PCT Pub. Date: Oct. 12, 2023

(65) Prior Publication Data
US 2025/0213248 A1 Jul. 3, 2025

(30) Foreign Application Priority Data
Apr. 8, 2022 (CN) .......................... 202210370014.7

(51) Int. Cl.
*A61B 17/072* (2006.01)
(52) U.S. Cl.
CPC .. *A61B 17/072* (2013.01); *A61B 2017/07264* (2013.01)

(58) Field of Classification Search
CPC ..................... A61B 17/072; A61B 2017/07264
See application file for complete search history.

(56) References Cited

U.S. PATENT DOCUMENTS

| | | | |
|---|---|---|---|
| 4,354,628 A | 10/1982 | Green | |
| 4,527,724 A | 7/1985 | Chow et al. | |

(Continued)

FOREIGN PATENT DOCUMENTS

| | | | |
|---|---|---|---|
| CN | 102835983 B | 8/2016 | |
| EP | 0537572 B1 | 6/1999 | |

(Continued)

OTHER PUBLICATIONS

International Search report and Written Opinion dated Jun. 29, 2023, for International Application No. PCT/IB2023/053477, 10 pages.

(Continued)

*Primary Examiner* — Nathaniel C Chukwurah
(74) *Attorney, Agent, or Firm* — FBT Gibbons LLP

(57) ABSTRACT

An open linear stapler includes an end effector located at a distal side. The end effector includes a substantially U-shaped stationary jaw located at the distal side and a movable jaw movable relative to the stationary jaw to clamp tissue therebetween. A surface of the stationary jaw opposes the movable jaw and includes an anvil. The movable jaw is configured to receive a staple cartridge. The stationary jaw includes two substantially U-shaped outer anvil clamping plates, and a distal surface of the anvil is fixedly connected to proximal surfaces of the distal ends of the outer anvil clamping plates. The stapler can be more easily inserted into the patient's body and provide a larger free space.

20 Claims, 15 Drawing Sheets

(56) References Cited

U.S. PATENT DOCUMENTS

| | | | |
|---|---|---|---|
| 4,568,009 A | 2/1986 | Green | |
| 4,573,622 A | 3/1986 | Green et al. | |
| 4,585,153 A | 4/1986 | Failla | |
| 4,715,520 A * | 12/1987 | Roehr, Jr. | A61B 17/072 227/19 |
| 4,805,523 A | 2/1989 | Stuckey et al. | |
| 4,805,823 A | 2/1989 | Rothfuss | |
| 4,848,637 A | 7/1989 | Pruitt | |
| 4,930,503 A | 6/1990 | Pruitt | |
| 5,439,155 A | 8/1995 | Viola | |
| 5,462,215 A | 10/1995 | Viola et al. | |
| 5,547,117 A | 8/1996 | Hamblin et al. | |
| 5,641,111 A * | 6/1997 | Ahrens | A61B 17/072 227/19 |
| 5,810,240 A * | 9/1998 | Robertson | A61B 17/072 227/176.1 |
| 5,919,198 A | 7/1999 | Graves et al. | |
| 6,805,273 B2 | 10/2004 | Bilotti et al. | |
| 6,817,508 B1 * | 11/2004 | Racenet | A61B 17/072 227/176.1 |
| 8,328,064 B2 | 12/2012 | Racenet et al. | |
| 11,202,628 B2 | 12/2021 | Posey et al. | |
| 2004/0084505 A1 | 5/2004 | Bilotti et al. | |
| 2005/0139629 A1 | 6/2005 | Schwemberger et al. | |
| 2011/0226837 A1 | 9/2011 | Baxter, III et al. | |
| 2013/0206813 A1 | 8/2013 | Nalagatla | |
| 2015/0119904 A1 | 4/2015 | Ji et al. | |
| 2017/0281177 A1 | 10/2017 | Harris et al. | |
| 2020/0205810 A1 | 7/2020 | Posey et al. | |
| 2020/0205811 A1 | 7/2020 | Posey et al. | |
| 2020/0337699 A1 * | 10/2020 | Rector | A61B 17/072 |
| 2020/0337700 A1 | 10/2020 | Hontz et al. | |
| 2021/0186495 A1 | 6/2021 | Shelton, IV et al. | |
| 2022/0000479 A1 | 1/2022 | Shelton, IV et al. | |
| 2022/0142641 A1 | 5/2022 | Wang | |
| 2024/0225642 A1 | 7/2024 | Ren et al. | |
| 2025/0049436 A1 | 2/2025 | Wang | |
| 2025/0195065 A1 | 6/2025 | Yang et al. | |
| 2025/0204912 A1 | 6/2025 | Yang et al. | |
| 2025/0213248 A1 | 7/2025 | Zhang et al. | |
| 2025/0213250 A1 | 7/2025 | Ding et al. | |
| 2025/0228559 A1 | 7/2025 | Ding et al. | |
| 2025/0255605 A1 | 8/2025 | Yang et al. | |

FOREIGN PATENT DOCUMENTS

| | | |
|---|---|---|
| EP | 1552791 B1 | 6/2009 |
| EP | 1550411 B1 | 7/2009 |
| EP | 3476310 A1 | 5/2019 |
| EP | 3225179 B1 | 4/2020 |
| EP | 3673826 A1 | 7/2020 |
| EP | 3730070 A1 | 10/2020 |
| EP | 3730069 B1 | 7/2023 |
| EP | 3730068 B1 | 9/2023 |
| EP | 3636166 B1 | 3/2024 |
| WO | 2021/168704 A1 | 9/2021 |
| WO | 2021/168726 A1 | 9/2021 |

OTHER PUBLICATIONS

International Search Report and Written Opinion dated Jul. 4, 2023 for Application No. PCT/IB2023/053467, 9 pages.
International Search Report and Written Opinion dated Jul. 12, 2023 for Application No. PCT/IB2023/053469, 9 pages.
International Search Report and Written Opinion dated Jul. 21, 2023 for Application No. PCT/IB2023/053476, 9 pages.
International Search Report and Written Opinion dated Jul. 5, 2023 for Application No. PCT/IB2023/053478, 9 pages.
International Search Report and Written Opinion dated Jul. 5, 2023 for Application No. PCT/IB2023/053481, 10 pages.
International Search Report and Written Opinion dated Jul. 14, 2023 for Application No. PCT/IB2023/053483, 12 pages.

* cited by examiner

81'

8'

F G 5

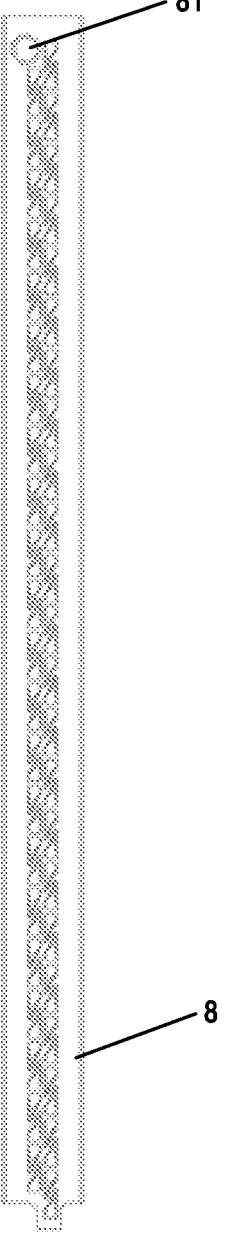
FI G 6

OPEN LINEAR STAPLER

FIELD

The present disclosure relates to an open linear stapler, particularly an open linear stapler that can be more easily inserted into a patient's body and provide a larger free space during surgery.

BACKGROUND

Nowadays, in medical field a stapler is a medical instrument commonly used in surgery. The stapler can be clamped onto one or more tissue layers of a patient during surgery, and staples fired from the stapler can seal the tissue layer(s) adjacent the staples. A typical stapler includes an end effector which can be inserted into the patient's body and positioned relative to the tissue to be sealed. The end effector includes a pair of elongated jaw members cooperating with each other, where one of the jaw members includes a staple cartridge that receives therein at least two rows of staples, and the other includes an anvil that has staple forming pockets aligned with the rows of staples in the staple cartridge. In general, the stapler can further include a push rod which can slide relative to the jaw members to fire staples sequentially or simultaneously from the staple cartridge via a cam surface on a wedge slide on the push rod. The cam surface can actuate one or more staple drivers associated with staples carried by the staple cartridge, so as to push the staples against the anvil and form rows of staples in the tissue clamped between the jaw members. The rows of staples may be arranged as linear rows and/or arc rows for stapling patient's tissue sequentially or simultaneously in a predetermined pattern. The stapler can be classified as a cavity stapler and an open stapler, where the cavity stapler is suitable for minimally invasive surgery, such as endoscopic or laparoscopic surgery, and thus has a small end effector. According to the above classification, the present disclosure relates to an open stapler where rows of staples are arranged linearly, namely an open linear stapler.

However, the existing open linear stapler has two obvious disadvantages. First of all, referring to FIG. 1, the anvil in the existing stapler is a U-shaped anvil sheathed outside of the outer anvil clamping plates provided with the anvil, canusing the stationary jaw of the stapler too thick and more tissue of the patient to be dissociated. Secondly, referring to FIG. 2, the tissue retaining pin hole on the anvil of the stapler is located at the topmost end of the anvil, making it unlikely to dispose a staple forming pocket there, or even more unlikely to arrange a staple at the corresponding position. In the condition, there is a possibility that the sealed tissue of the patient leaks out during the stapling process at the position.

To this end, there arises a need for a novel open linear stapler which can reduce the thickness of the end effector of the stapler to enable easier insertion into a patient's body during surgery while preventing the anvil from moving relative to the jaws when the stapler is in use, and lower the leakage risk of the sealed tissue.

SUMMARY

The present disclosure provides an open linear stapler. The specific content is provided below.

According to an aspect of the present disclosure, there is provided an open linear stapler, comprising an end effector located at a distal side, wherein: the end effector comprises a substantially U-shaped stationary jaw located at the distal side and a movable jaw movable relative to the stationary jaw to clamp tissue therebetween, a surface of the stationary jaw opposing the movable jaw comprises an anvil, and the movable jaw is configured to receive a staple cartridge, characterized in that: the stationary jaw comprises two substantially U-shaped outer anvil clamping plates, and a distal surface of the anvil is fixedly connected to proximal surfaces of the distal ends of the outer anvil clamping plates.

According to a further aspect of the open linear stapler of the present disclosure, at least one bending portion is disposed on outer surfaces of the two substantially U-shaped outer anvil clamping plates to allow the two outer anvil clamping plates to bend towards each other, thereby reducing a distance between the two outer anvil clamping plates.

According to a further aspect of the open linear stapler of the present disclosure, the movable jaw is provided thereon with a tissue retaining pin, the anvil of the stationary jaw is provided thereon with a tissue retaining pin hole at a position corresponding to that of the tissue retaining pin, and the tissue retaining pin hole is located at an upper end of the anvil in a vertical direction and arranged offset in a transverse direction.

According to a further aspect of the open linear stapler of the present disclosure, the open linear stapler further comprises an inner anvil clamping plate located between respective distal ends of the two outer anvil clamping plates.

According to a further aspect of the open linear stapler of the present disclosure, a clearance is provided between the inner anvil clamping plate and the anvil.

According to a further aspect of the open linear stapler of the present disclosure, the fixed connection is achieved by welding or bonding.

According to a further aspect of the open linear stapler of the present disclosure, the inner anvil clamping plate is made from plastic or metal approved for use in medical instruments.

According to a further aspect of the open linear stapler of the present disclosure, the plastic approved for use in medical instruments is Nylon 66.

According to a further aspect of the open linear stapler of the present disclosure, the metal approved for use in medical instruments is medical stainless steel.

According to a further aspect of the open linear stapler of the present disclosure, the outer anvil clamping plates are made from metal approved for use in medical instruments.

According to a further aspect of the open linear stapler of the present disclosure, the metal approved for use in medical instruments is medical stainless steel.

According to a further aspect of the open linear stapler of the present disclosure, the welding is laser welding, gas shielded welding, or friction stir welding.

According to a further aspect of the open linear stapler of the present disclosure, an adhesive used in bonding is an adhesive material approved for use in medical instruments.

According to a further aspect of the open linear stapler of the present disclosure, a coating layer is applied over the outer surface of the substantially U-shaped anvil.

The open linear stapler according to the present disclosure can solve the aforesaid problem existing in the prior art, which can achieve miniaturization of the stapler, provide the surgeon with a larger free space, and improve sealing effect to the tissue.

BRIEF DESCRIPTION OF THE DRAWINGS

FIG. 6 is a schematic diagram of an anvil of a stapler according to a third embodiment of the present disclosure.

Figure 1:
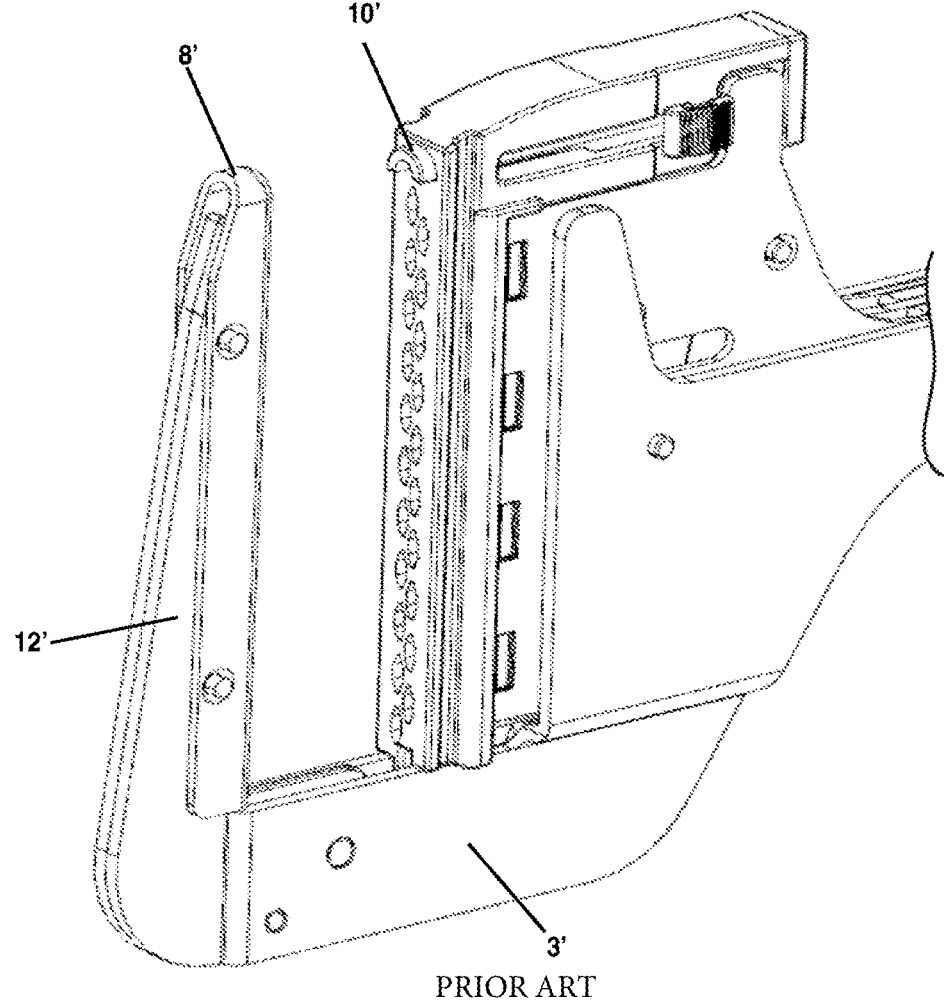
FIG. 1 is a schematic diagram of an end effector of an existing open linear stapler.

In the drawings, reference signs are listed below: 1—handle; 2—connecting rod; 3'/3—end effector; 4—firing trigger; 6—stationary jaw; 7—movable jaw; 8'/8—anvil; 81'/81—tissue retaining pin hole; 9—staple cartridge; 10'/10—tissue retaining pin; 11—inner anvil clamping plate; 12'/12—outer anvil clamping plate; and 121/122—bending portion.

DETAILED DESCRIPTION OF EMBODIMENTS

Reference will now be made to the drawings to further describe the technical solution of the present disclosure through specific embodiments, but the present disclosure is not confined to those embodiments. Description on some examples of the present disclosure below should not be used to limit the scope of the present disclosure. Through the description below which is offered in an exemplary manner, other examples, features, aspects, implementation solutions and advantages will become more apparent to those skilled in the art, and an optimum way is supposed to be employed for implementing the present disclosure. It will be appreciated that the present disclosure covers other distinct and apparent aspects, and those aspects do not depart from the present disclosure. Therefore, the drawings and the illustration should be considered as examples in substance, rather than restrictions.

In addition, any one(s) of the teachings, expressions, implementation solutions, examples, and the like as described herein may be combined with any other(s) therein. Accordingly, the teaching, expressions, implementation solutions, embodiments provided below should not be taken as being independent from each other. Various appropriate manners combined according to the teachings will become obvious to those skilled in the art. Such modifications and variations are intended to be covered within the scope defined by the claims appended hereinafter.

For clarity, the terms "proximal side" and "distal side" are used herein with reference to an operator manipulating the surgical instrument or robot. The term "proximal side" refers to an element position close to the operator manipulating the surgical instrument or robot and away from the surgical end effector 3 of the surgical instrument. The term "distal side" refers to an element position close to the surgical end effector 3 of the surgical instrument and away from the operator manipulating the surgical instrument or robot. It will be further appreciated that, for convenience and clarity, spatial terms such as "vertical", "horizontal", "up", "down", "front" and "rear" may be used herein with respect to the drawings. However, surgical instruments are used in many orientations and positions, and these terms are not intended to be limiting and/or absolute.

Hereinafter, reference will be made to FIGS. 3-6 to describe in detail the open linear stapler according to the present disclosure.

Figure 3:
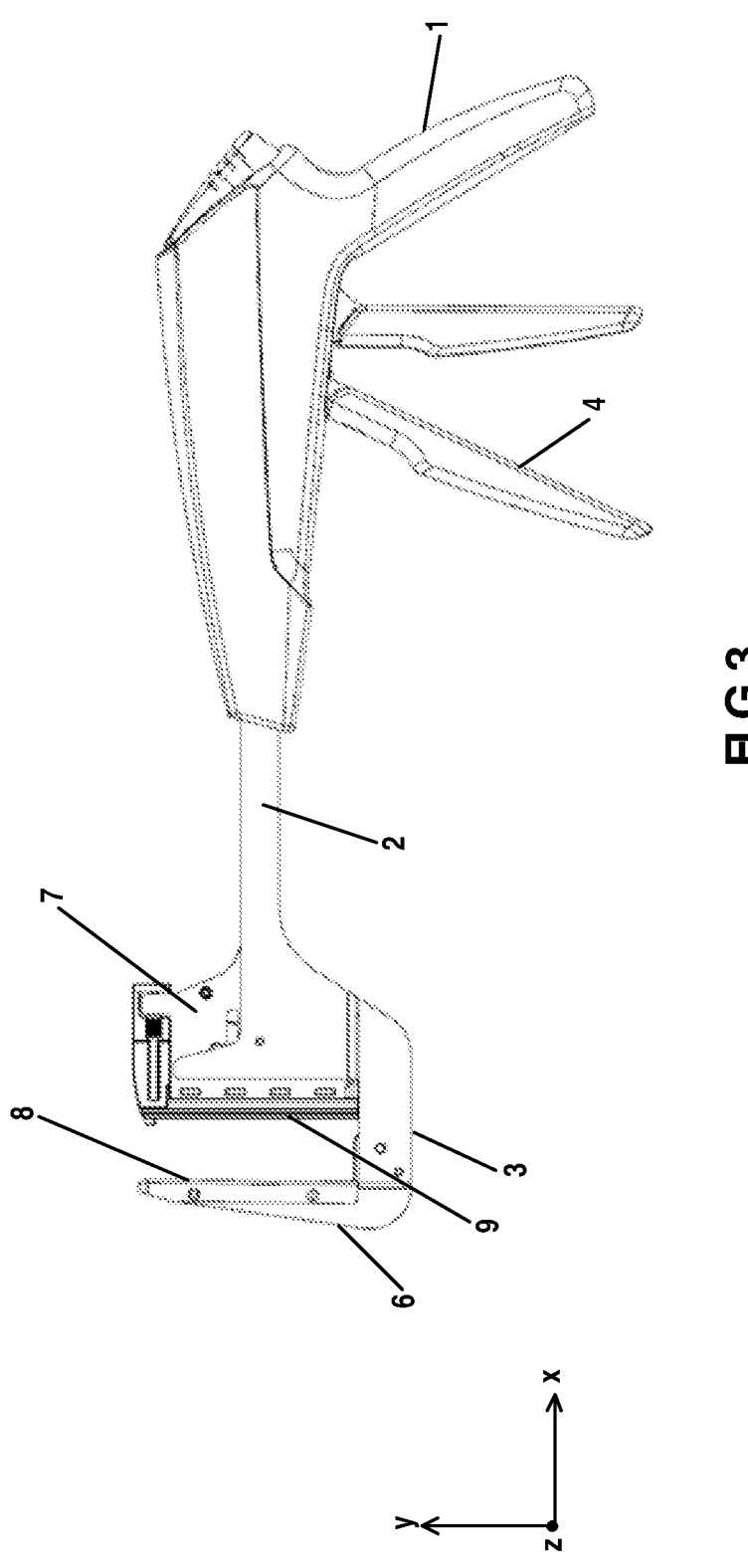
FIG. 3 is a schematic diagram of a basic configuration of a stapler according to the present disclosure.

With reference to FIG. 3, the basic structure of the stapler according to the present disclosure will be described first. The stapler according to the present disclosure is mainly comprised of a main body and a firing member. According to the sequence from the proximal side to the distal side, the main body includes a handle 1, a connecting rod 2, and an end effector 3. The firing member includes a firing trigger 4 and a push rod 5, where the push rod 5 may be designed as a conventional long push rod, or may be designed as a short push rod. The end effector 3 is mainly comprised of two jaws including a substantially U-shaped stationary jaw 6 and a movable jaw 7 movable relative to the stationary jaw, where the stationary jaw 6 includes an anvil 8, the movable jaw 7 includes a staple cartridge 9, the movable jaw 7 is provided thereon with a tissue retaining pin 10, and the anvil 8 of the stationary jaw 6 is provided thereon with a tissue retaining pin hole 81 at a position corresponding to that of the tissue retaining pin 10. The connecting rod 2 is configured to connect the handle 1 with the end effector 3. Although the present disclosure will be described in the condition that the stationary jaw 6 is disposed at a distal side while the movable jaw 7 is located at a proximal side, it is to be understood by those skilled in the art that the present disclosure is also applicable to the situation where the stationary jaw 6 is disposed at the proximal side while the movable jaw 7 is located at the distal side.

For ease of description, a three-dimensional coordinate system is depicted in FIG. 3, where the X-direction represents the horizontal direction, the Y-direction denotes the vertical direction, and the Z-direction is the transverse direction. The coordinate system and the three directions as mentioned above can be applied to other drawings of the present disclosure.

First Embodiment

Figure 4:
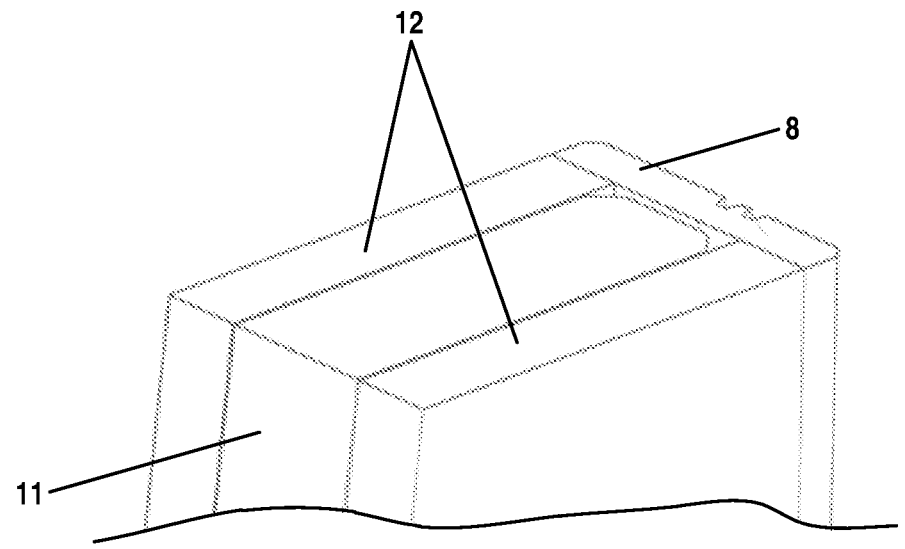
FIG. 4 is a schematic diagram of a stationary jaw of an end effector of a stapler according to a first embodiment of the present disclosure.

The first embodiment will be described below. FIG. 4 is a schematic diagram of a substantially U-shaped stationary jaw 6 of the end effector 3 of the stapler according to the first embodiment of the present disclosure. As shown in FIG. 4, the stationary jaw 6 according to the present disclosure includes a hook member that looks like a hook as it extends distally leftwards along the horizontal direction from the bottom of the main body of the stapler (i.e., the lower part in the Y direction in FIG. 3) to the distalmost end of the end effector 3, and then extends upwards along the vertical direction. The hook member includes an inner anvil clamping plate 11 located in the middle and two outer anvil clamping plates 12 disposed at respective outer sides of the inner anvil clamping plate 11 in the transverse direction. The inner anvil clamping plate 11 is preferably made from plastics approved for use in medical instruments, particularly nylon, more particularly the medical material Nylon 66. Of course, the inner anvil clamping plate 11 may also be made from metal approved for use in medical instruments, such as medical stainless steel. The anvil 8 and the outer anvil clamping plates 12 are made from metal approved for use in medical instruments, preferably medical stainless steel.

At the proximal end of the stationary jaw 6, the anvil 8 is fixedly connected to the proximal surfaces of the distal ends of the substantially U-shaped outer anvil clamping plates 12 by welding. Since a large amount of heat is generated during welding, the anvil 8 is not in direct contact with the inner anvil clamping plate 11. Instead, as can be clearly seen from FIG. 4, a minor clearance is provided between the anvil 8 and the inner anvil clamping plate 11, from which the heat generated during welding will not be transferred directly to the inner anvil clamping plate 11.

For the welding applied between the anvil 8 and the outer anvil clamping plate 12, laser welding is preferred. In addition, gas shielded welding or friction stir welding may also be employed.

In addition to welding, the anvil 8 and the outer anvil clamping plate 12 may be fixedly connected through other methods, such as adhesion, where the adhesive material for adhesion should be approved for use in medical instruments.

In terms of shape, the anvil 8 is aligned with the inner anvil clamping plate 11 and the outer anvil clamping plates 12 in the transverse and vertical directions. In other words, as observed from two side surfaces of the end effector 3 in the transverse direction and from the top to the bottom in the vertical direction, respective surfaces formed by the anvil 8 together with the internal anvil clamping plate 11 and the outer anvil clamping plates 12, are smooth, rather than bumpy. With the arrangement, when observed from the firing orientation along the horizontal direction, the hook member concealed under the anvil 8 and thus imperceptible, as shown in FIG. 4.

By contrast, the anvil 8' in the prior art as shown in FIG. 1, which has a U-shape, is sheathed outside the hook member and fixedly connected to the latter via a rivet. In this connection method, the U-shaped anvil 8' and the hook member cannot form a substantially rigid one-piece member. Therefore, during the use of the stapler, after the firing trigger (not shown) has been triggered, the firing force is transmitted from the anvil 8' first to the rivet pin between the anvil 8' and the outer anvil clamping plates 12', and then to the outer anvil clamping plates 12'. During this process, the firing force is transmitted for a long distance.

In the first embodiment of the present disclosure, the anvil 8 is directly welded onto the two outer anvil clamping plates 12 such that the anvil 8 and the hook member form a substantially rigid one-piece member. In this way, when the stapler is in use and after the firing trigger 4 has been triggered, the firing force is directly transmitted from the anvil 8 to the outer anvil clamping plates 12 as an effect of the force of the push rod, thus resulting in short-distance transmission of the force. The outer anvil clamping plates 12 configured in the above manner according to the present disclosure has a high load capacity.

Second Embodiment

Figure 5:
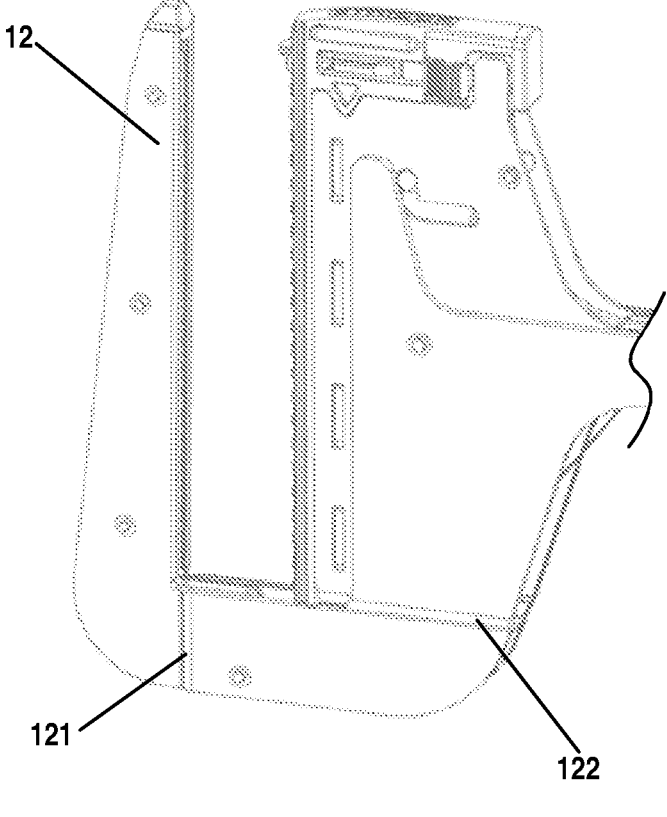
FIG. 5 is a schematic diagram of an end effector of a stapler according to a second embodiment of the present disclosure.

The second embodiment of the present disclosure will be described below. FIG. 5 is a schematic diagram of an end effector 3 of the stapler according to the second embodiment of the present disclosure. As can be clearly seen from FIG. 5, two bending portions are provided on the outer surface of the outer anvil clamping plates 12, causing the two outer anvil clamping plate 12 to bend towards each other and thus reduce the distance between the two outer anvil clamping plates 12. Wherein, a bending portion 121 in the vertical direction is disposed proximal to the distal end, and a bend portion 122 in the horizontal direction is located at the proximal side. Although not shown, it will be appreciated by those skilled in the art that identical bending portions are provided at the other outer anvil clamping plate 12 located at the other side, which are unobservable in FIG. 5. The arrangement of the two bending portions shortens the distance between the two outer anvil clamping plates 12 and further reduces the dimension of the end effector 3 in the transverse direction, thereby implementing miniaturization of the stapler. As such, the stapler according to the present disclosure can be easily inserted into some critical parts of a patient's body, like deep abdomen. Although the above embodiment where the outer anvil clamping plate 12 includes two bending portions is used herein is described, it is to be understood by those skilled in the art that only one bending portion can also accomplish the purpose of reducing the size of the end effector 3.

Third Embodiment

The third embodiment of the present disclosure will be described below. Reference is made to FIG. 6 which is a schematic diagram of an anvil 8 of the stapler according to the third embodiment of the present disclosure. At the upper end of the anvil 8 in the vertical direction, a tissue retaining pin hole 81 is disposed off-center (i.e., offset from a transverse center) in the transverse direction and configured to cooperate with a tissue retaining pin 10 such that the movable jaw 7 and the stationary jaw 6 are positioned during stapling. In other words, the staple cartridge 9 and the anvil 8 are positioned precisely during stapling to guarantee that staples fired from the staple cartridge 9 are aligned with the staple forming pockets on the anvil 8 one by one.

Figure 2:
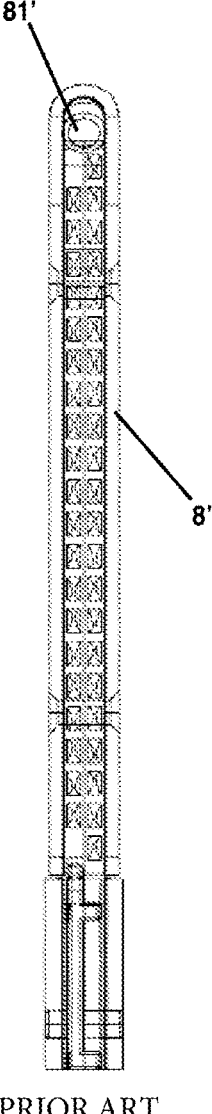
FIG. 2 is a schematic diagram of an anvil of the end effector of the existing open linear stapler.

Corresponding to the third embodiment of the present disclosure, FIGS. 1 and 2 illustrate an anvil 8' of an end effector 3' of an existing open linear stapler, where the tissue retaining pin hole 81' is positioned at the center of the anvil in the transverse direction although disposed at the upper end of the anvil 8' in the vertical direction. In the circumstance, a staple forming pocket cannot be disposed at this position, nor can a corresponding staple be provided. As such, a staple is missing at the position when stapling the patient's tissue. Through experiment, the inventors have noticed that sparse stapling is probably performed on patient's tissue at the distal end of the anvil 8' close to the tissue retaining pin 10', which probably leads to leakage.

According to the present disclosure, the tissue retaining pin hole 81 is disposed off-center, thereby enabling an additional staple forming pocket to be provided adjacent to the tissue retaining pin hole 81 at the upper end of the anvil 8 in the vertical direction. Although only one additional staple forming pocket is provided, the inventors have found through experiment that, as compared with the prior art where the tissue retaining pin hole 81 is disposed in the center, the present disclosure where the anvil 8 has a tissue retaining pin hole 81 disposed off-center can reduce the possibility of sparse stapling at the ends by 20%-30% and achieve a good stapling effect, for example, a good hemostasis effect.

In the third embodiment of the present disclosure, given the fact that the tissue retaining pin hole 81 is disposed off-center on the anvil 8, a clearance between the edge of the tissue retaining pin hole 81 and the edge of the pockets on the anvil should be greater than 0.010 inches, and the width of the anvil should be set to guarantee a sufficient distance between the edge of the tissue retaining pin hole 81 and the edge of the anvil. In the case, if the U-shape anvil 8 is still sheathed outside the hook member as in the prior art, the dimension of the stationary jaw 6 of the end effector 3 in the transverse direction will be increased significantly, thus hindering insertion of the stapler into the patient's body. By contrast, if the anvil 8 is fixedly connected to the proximal end of the outer anvil clamping plate 12 by welding as described in the first embodiment of the present disclosure, the dimension of the end effector 3 of the stapler in the transverse direction will be thinned. For example, the thickness of the distal end of the anvil system is 0.251 inches.

In addition, in order to prevent the substantially U-shaped outer anvil clamping plate from entangling with the tissue, a coating can be applied over the outer surface of the substantially U-shaped anvil to thus improve the smoothness of the anvil.

From the foregoing description, those skilled in the art would have a clear picture about the invention conception and the specific technical means of the present disclosure. The open linear stapler according to the present disclosure can reduce the transverse thickness of the hook member system, thereby allowing easier insertion into a patient's body during surgery and enabling a simpler anvil manufacturing process. During firing, the outer anvil clamping plate has a better load-bearing capacity. No clearance exists between the anvil and the outer anvil clamping plate, making it impossible for the anvil to move relative to the outer anvil clamping plate in use. Moreover, the staple additionally provided beside the tissue retaining pin hole disposed off-center can lower the leakage risk of the tissue to be sealed around the tissue retaining pin.

It will be appreciated by those skilled in the art that the three embodiments of the present disclosure as discussed above can be implemented alone or in combination.

In addition, the present disclosure also covers the following improved embodiments.

Figure 7A:
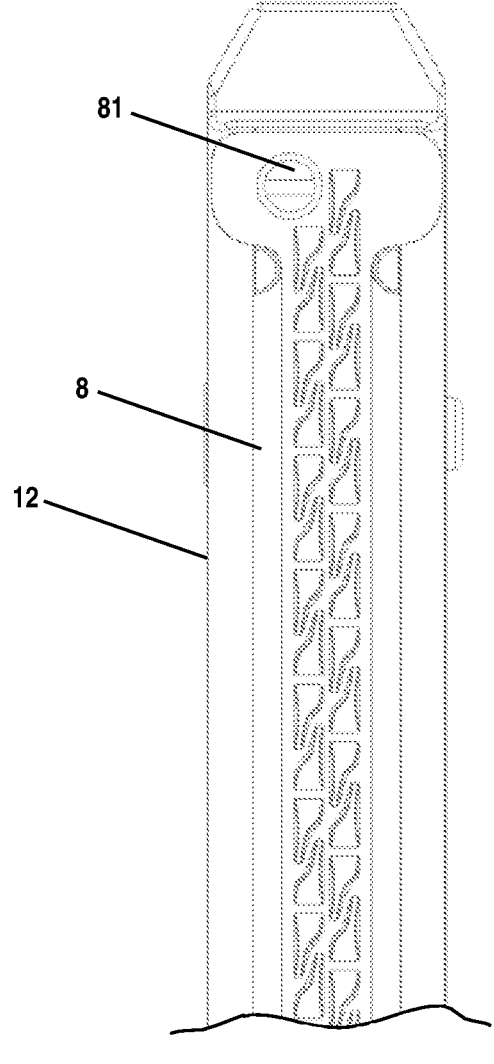
FIGS. 7A-7C are schematic diagrams of an anvil of a stapler according to another embodiment of the present disclosure.
Figure 7B:
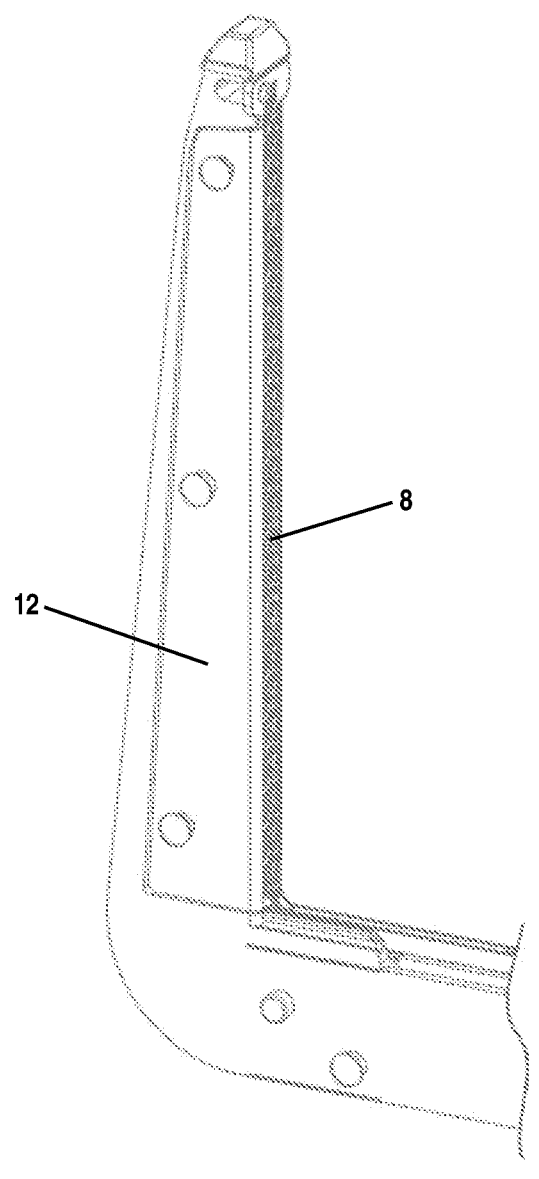
Figure 7C:
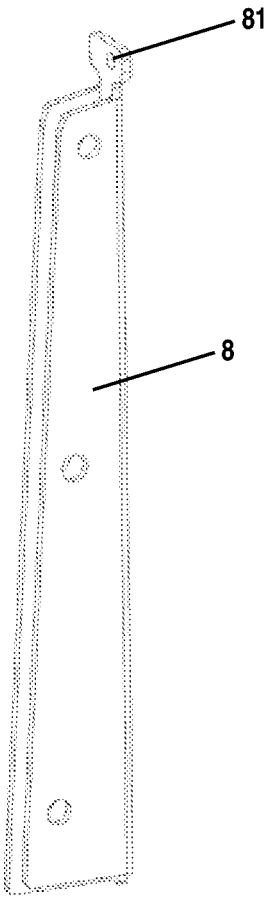

FIGS. 7A-7C illustrate an anvil in the first improved embodiment of the present disclosure. Wherein, the main body of the anvil is of a U-shape; the anvil surface is provided with staple forming pockets; the anvil top has a different shape than the main body, which is flat-sheet like, rather than U-shaped, as clearly shown in the drawings. The objective of such arrangement is to acquire the minimum width of the anvil. In the circumstance, the main body of the anvil is designed in a U shape, and the upper end part of the anvil is a sheet disposed on the outer anvil clamping plates and protruding from the latter in the Z direction (i.e., the transverse direction) to spare a sufficient space for arrangement of the off-center tissue retaining pin hole on the sheet. The anvil according to the improved embodiment provides a large space for the off-center tissue retaining pin hole, thereby facilitating processing. The outer anvil clamping plates covered by the anvil have a support function in use. The main body of the anvil is designed in a U-shape which contributes to a good stress behavior of the anvil, and the end sheet of the anvil can provide a larger space for the anvil end, which is particularly suitable for arrangement of an off-center tissue retaining pin hole.

Figure 8A:
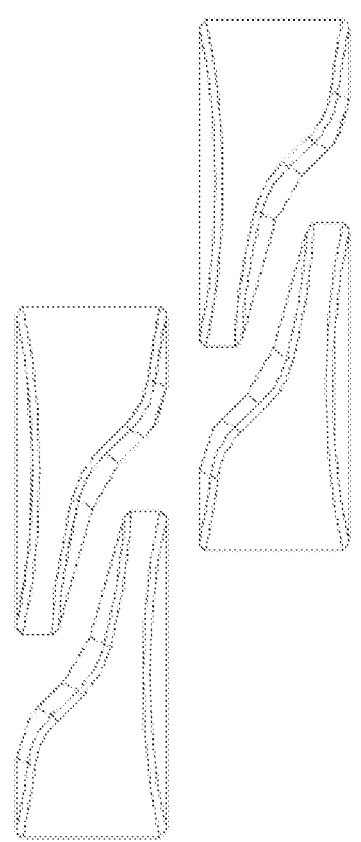
FIG. 8A is a schematic diagram of an arrangement of staple forming pockets according to the prior art.
Figure 8B:
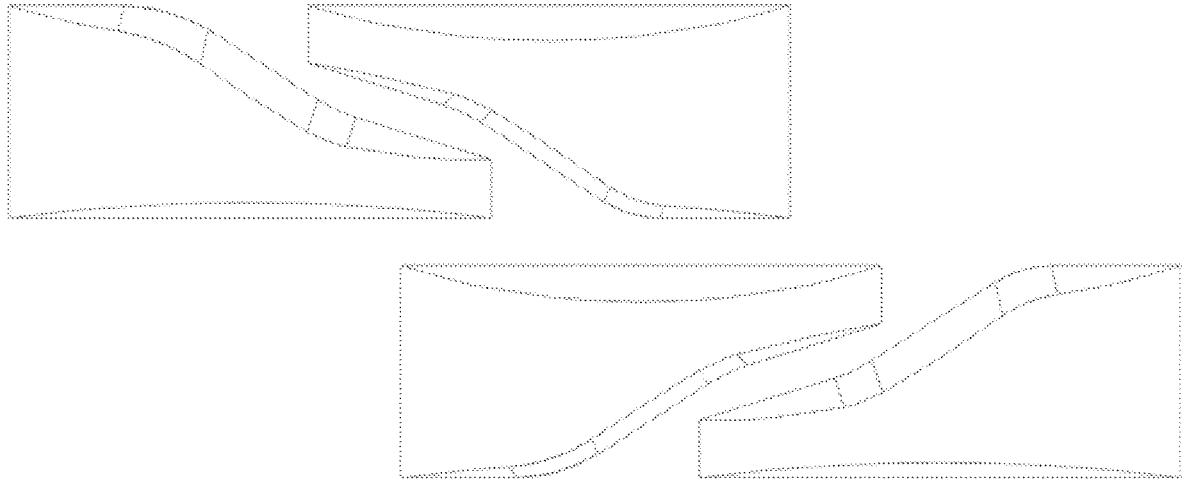
FIG. 8B is a schematic diagram of an arrangement of staple forming pockets of a stapler according to a further embodiment of the present disclosure.

FIGS. 8A-8B illustrate a second improved embodiment of the present disclosure. The improved embodiment relates to a pattern arrangement of 3D staple forming pockets on an anvil. A 3D staple forming pocket is comprised of two small pockets, i.e., every two small staple forming pockets form a large 3D staple forming pocket. As shown in FIG. 8A, the existing 3D staple forming pockets are arranged in parallel, i.e., two rows of 3D staple forming pockets forming two staple sutures copy each other in arrangement, with a passage formed therebetween. In the case, torque is generated when pressure within the patient's body acts on the staples, and clearance in parallel among the staples is disadvantageous for leakage-proof. The improved embodiment according to the present disclosure is depicted in FIG. 8B, where the left and right rows of 3D staple pockets are staggerly arranged along the Y direction after being put mirror symmetrically with the Y-direction as a symmetry axis. Those skilled in the art should understand that the staggered arrangement should ensure that at least a part of the corresponding 3D staple pockets of the two rows of 3D staple pockets overlap in the Z direction. In the arrangement, a balanced force is generated for each element, enabling the arrangement to achieve a better stapling effect. Wherein, the staples may be made from titanium.

Figure 9A:
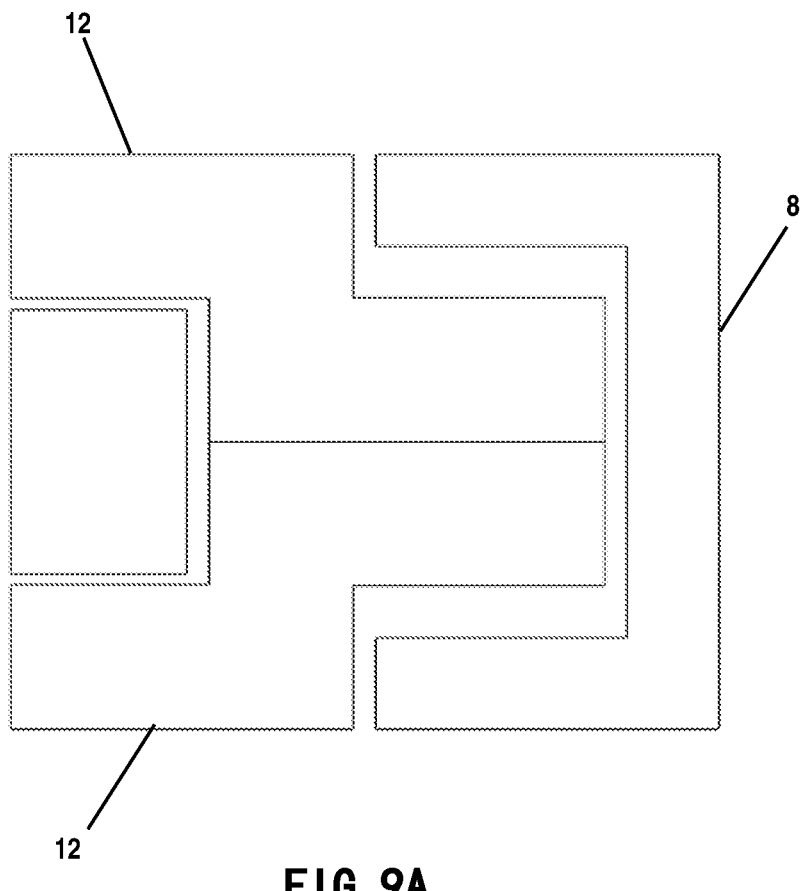
FIGS. 9A-9B are schematic diagrams of a stationary jaw of a stapler according to a still further embodiment of the present disclosure.
Figure 9B:
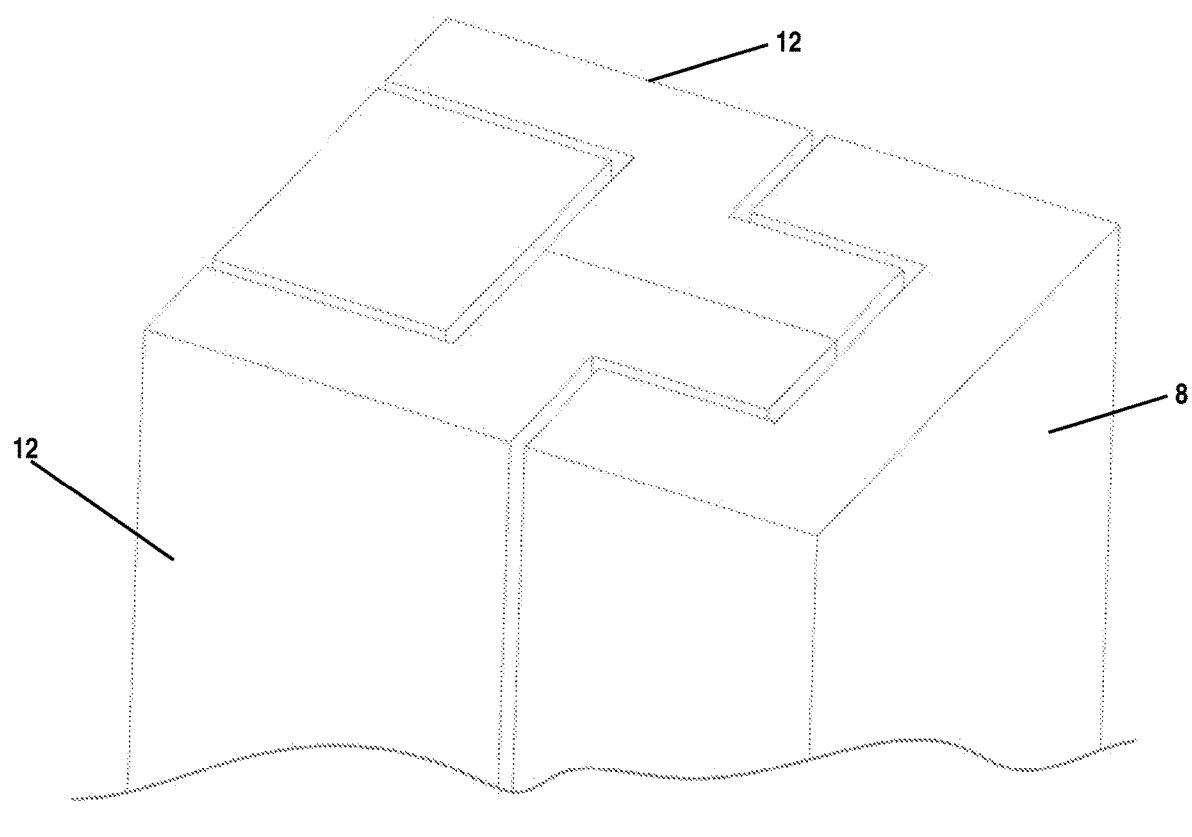

A third improved embodiment of the present disclosure will be described below. As shown in FIGS. 9A and 9B, in the embodiment, the two outer anvil clamping plates are not flat sheet members but exhibit in a curved shape as seen from the horizontal section. If measured from the Z direction (i.e., the transverse direction), a clearance between the two outer anvil clamping plates formed at the proximal side is small while the counterpart formed at the distal side is large. The U-shaped anvil covers the proximal ends of the two outer anvil clamping plates, respectively, and the proximal surfaces of the two outer anvil clamping plates support the rear surface of the anvil. At the distal ends of the outer anvil clamping plates, a plastic member is disposed between the two outer anvil clamping plates to fill the clearance therebetween. A pin extending transversely is used to secure the anvil onto the outer anvil clamping plates. In the surgical stapler according to this embodiment, the stationary jaw has a smaller thickness, the anvil has a smaller width, and the outer anvil clamping plates in a curved shape can reinforce the rigidity of the anvil system as a whole.

Figure 10A:
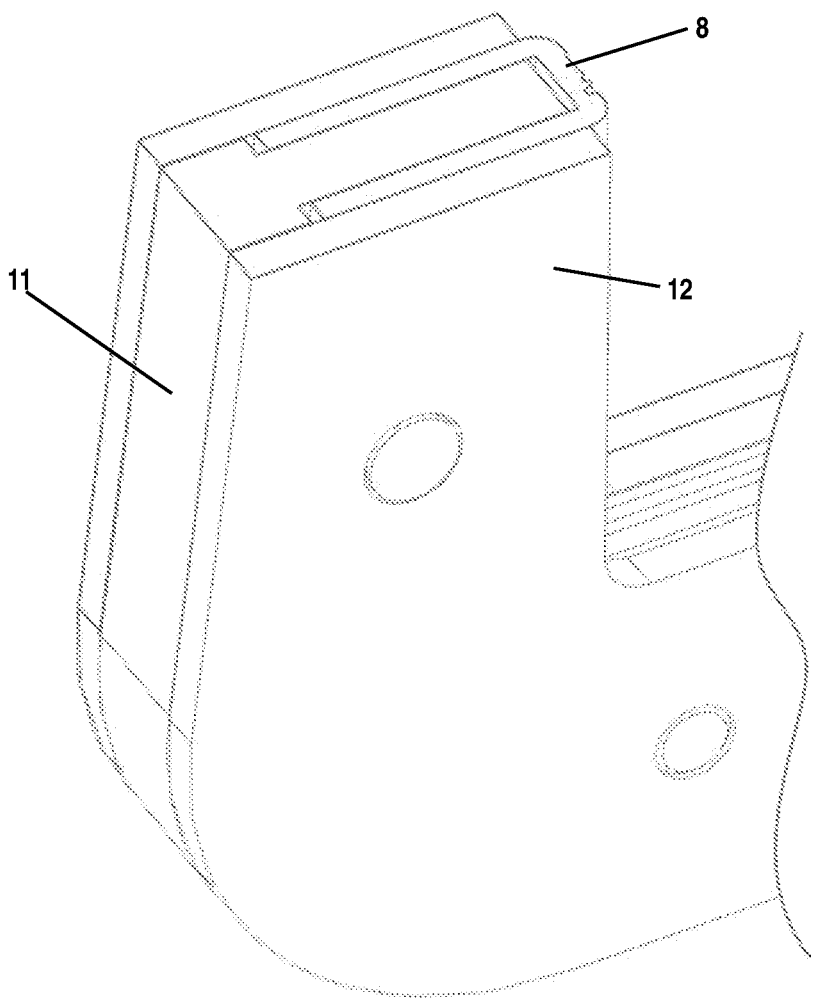
FIGS. 10A-10B are schematic diagrams of a stationary jaw of a stapler according to a still further embodiment of the present disclosure.
Figure 10B:
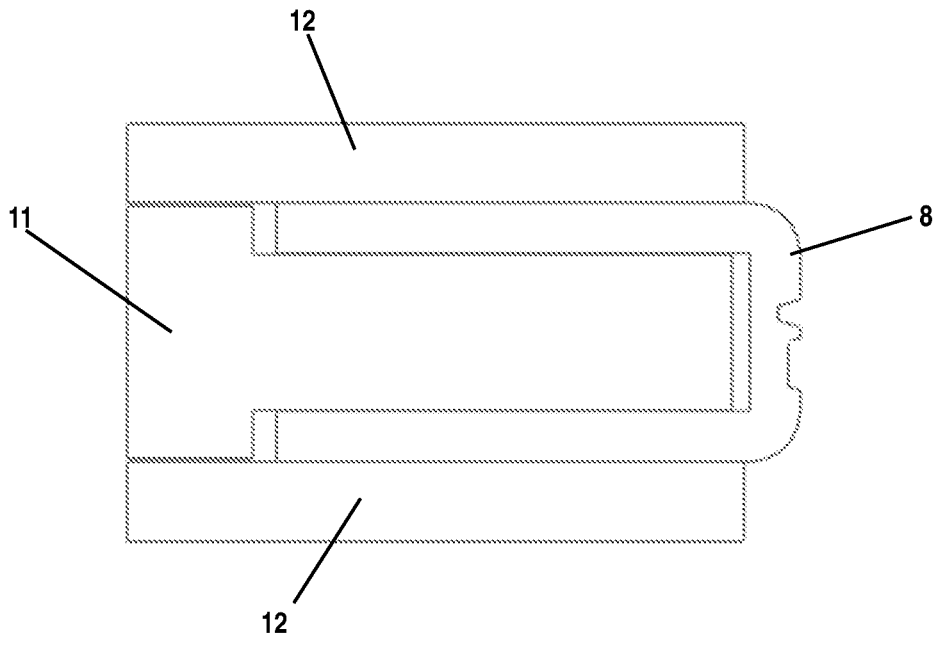

A fourth improved embodiment of the present disclosure will be described below. In FIGS. 10A and 10B, as seen from the horizontal section, the main body of the anvil is of a U shape and sleeved onto the inner anvil clamping plate. The inner anvil clamping plate has a T shape and is in nesting engagement with the main body of the anvil mutually. The two outer anvil clamping plates cover the two sides of the anvil and the inner anvil clamping plate. The top of the anvil is sheet like and covers the outside of the outer anvil clamping plates to spare enough room for an off-center tissue retaining pin hole at the top sheet of the anvil. As shown in FIG. 10B, the anvil protrudes from the outer anvil clamping plates in the X direction (i.e., the horizontal direction), thereby forming a height difference between the surfaces of the anvil and outer anvil clamping plates. The height difference provides a blade cutting site for cutting tissue for the surgeon.

The embodiments as described herein are provided merely as examples for illustrating spirits of the present disclosure. Without departing from the spirits of the present disclosure, those skilled in the art are allowed to make various modifications or additions to, or substitutions for the embodiments as disclosed herein, and the modifications, additions or substitutions shall all fall into the protection scope defined by the appended claims.

We claim:

1. An open linear stapler, comprising an end effector located at a distal side, wherein:

(a) the end effector comprises a substantially U-shaped stationary jaw located at the distal side and a movable jaw movable relative to the stationary jaw to clamp tissue therebetween, a surface of the stationary jaw opposing the movable jaw comprising an anvil having a first lateral-most surface, and the movable jaw being configured to receive a staple cartridge, (b) the stationary jaw comprises two substantially U-shaped outer anvil clamping plates, at least one of the two substantially U-shaped outer anvil clamping plates having a second lateral-most surface, and a distal surface of the anvil is fixedly connected to proximal surfaces of the distal ends of the outer anvil clamping plates, and (c) the first lateral-most surface of the anvil laterally extends at most up to the second lateral-most surface of the at least one of the two substantially U-shaped outer anvil clamping plates.

2. The open linear stapler of claim 1, wherein at least one bending portion is disposed on outer surfaces of the two substantially U-shaped outer anvil clamping plates, respectively, to allow the two outer anvil clamping plates to bend towards each other, thereby reducing a distance between the two outer anvil clamping plates.

3. The open linear stapler of claim 1, wherein the movable jaw is provided thereon with a tissue retaining pin, the anvil of the stationary jaw is provided thereon with a tissue retaining pin hole at a position corresponding to that of the tissue retaining pin, and the tissue retaining pin hole is located at an upper end of the anvil in a vertical direction and arranged offset in a transverse direction.

4. The open linear stapler of claim 1, wherein the end effector further comprises an inner anvil clamping plate located between respective distal ends of the two outer anvil clamping plates.

5. The open linear stapler of claim 4, wherein a clearance is provided between the inner anvil clamping plate and the anvil.

6. The open linear stapler of claim 4, wherein the inner anvil clamping plate comprises plastic or metal.

7. The open linear stapler of claim 6, wherein the plastic comprises Nylon 66.

8. The open linear stapler of claim 6, wherein the metal comprises stainless steel.

9. The open linear stapler of claim 1, further comprising a weld or bond providing the fixed connection.

10. The open linear stapler of claim 9, wherein the weld comprises a laser weld, a gas shielded weld, or a friction stir weld.

11. The open linear stapler of claim 9, wherein the bond comprises an adhesive material.

12. The open linear stapler of claim 1, wherein the outer anvil clamping plates comprise metal.

13. The open linear stapler of claim 12, wherein the metal of the outer anvil clamping plates comprises stainless steel.

14. The open linear stapler of claim 1, the anvil including an outer surface, the open linear stapler further comprising a coating over the outer surface of the anvil.

15. An open linear stapler, comprising an end effector located at a distal side, wherein:

the end effector comprises a substantially U-shaped stationary jaw located at the distal side and a movable jaw movable relative to the stationary jaw to clamp tissue therebetween, a surface of the stationary jaw opposing the movable jaw comprising an anvil, and the movable jaw being configured to receive a staple cartridge, wherein the stationary jaw comprises an inner anvil clamping plate, two substantially U-shaped outer anvil clamping plates, and a distal surface of the anvil is fixedly connected to proximal surfaces of the distal ends of the outer anvil clamping plates, wherein a gap is provided between the inner anvil clamping plate and the anvil.

16. The open linear stapler of claim 15, wherein at least one bending portion is disposed on outer surfaces of the two substantially U-shaped outer anvil clamping plates, respectively, to allow the two outer anvil clamping plates to bend towards each other, thereby reducing a distance between the two outer anvil clamping plates.

17. The open linear stapler of claim 15, wherein the movable jaw is provided thereon with a tissue retaining pin, the anvil of the stationary jaw is provided thereon with a tissue retaining pin hole at a position corresponding to that of the tissue retaining pin, and the tissue retaining pin hole is located at an upper end of the anvil in a vertical direction and arranged offset in a transverse direction.

18. The open linear stapler of claim 15, wherein the gap is formed between a distal surface of the anvil and a proximal surface of the inner anvil clamping plate.

19. The open linear stapler of claim 15, wherein the two substantially U-shaped outer anvil clamp plates collectively widen in a lateral direction at a distal portion of a U-shape relative to a proximal portion of the U-shape.

20. An open linear stapler, comprising an end effector located at a distal side, wherein:

(a) the end effector comprises a substantially U-shaped stationary jaw located at the distal side and a movable jaw movable relative to the stationary jaw to clamp tissue therebetween, a surface of the stationary jaw opposing the movable jaw comprising an anvil and the movable jaw being configured to receive a staple cartridge, the anvil including a coating and an outer surface, the coating being over the outer surface, (b) the stationary jaw comprises two substantially U-shaped outer anvil clamping plates, and a distal surface of the anvil is fixedly connected to proximal surfaces of the distal ends of the outer anvil clamping plates.

\* \* \* \* \*